United States Patent
Lakso et al.

(10) Patent No.: US 11,179,280 B2
(45) Date of Patent: Nov. 23, 2021

(54) ABSORBENT ARTICLE HAVING A TOPSHEET AND STANDING GATHERS EACH HAVING A SHEET MATERIAL WITH SPECIFIED STIFFNESS, SOFTNESS AND SMOOTHNESS PROPERTIES

(71) Applicant: SCA Hygiene Products AB, Gothenburg (SE)

(72) Inventors: Elisabeth Lakso, Gothenburg (SE); Carina Hedlund, Gothenburg (SE); Petter Andreassen, Gothenburg (SE); Morgan Swedberg, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 15/541,253

(22) PCT Filed: Jan. 2, 2015

(86) PCT No.: PCT/SE2015/000001
§ 371 (c)(1),
(2) Date: Jun. 30, 2017

(87) PCT Pub. No.: WO2016/108741
PCT Pub. Date: Jul. 7, 2016

(65) Prior Publication Data
US 2017/0348163 A1 Dec. 7, 2017

(51) Int. Cl.
*A61F 13/513* (2006.01)
*A61F 13/475* (2006.01)
(Continued)

(52) U.S. Cl.
CPC ...... *A61F 13/513* (2013.01); *A61F 13/15203* (2013.01); *A61F 13/4753* (2013.01);
(Continued)

(58) Field of Classification Search
CPC .......... A61F 13/15203; A61F 13/51121; A61F 13/513; A61F 2013/15357; A61F 13/4753;
(Continued)

(56) References Cited

U.S. PATENT DOCUMENTS 4,690,679 A    9/1987  Mattingly, III et al.
5,569,234 A *  10/1996 Buell ................ A61F 13/49009
                                                    604/396

(Continued)

FOREIGN PATENT DOCUMENTS

CN    1282234 A    1/2001
CN    102113936 A  7/2011
(Continued)

OTHER PUBLICATIONS

Notice of Allowance (Decision to Grant/ A Patent for Invention) dated Jun. 25, 2018, by the Federal Service for Intellectual property in Russian Patent Application No. 2017127463/(047360) and an English Translation of the Notice of Allowance. (16 pages).

(Continued)

*Primary Examiner* — Michele M Kidwell
(74) *Attorney, Agent, or Firm* — Buchanan Ingersoll & Rooney P.C.

(57) ABSTRACT

An absorbent article having a topsheet, a backsheet arranged on the garment-facing side, an absorbent core enclosed between the topsheet and the backsheet and a pair of standing gathers. The topsheet and the standing gathers comprise sheet materials with specified stiffness, softness and smoothness properties. The absorbent article may be a diaper or incontinence guard.

23 Claims, 2 Drawing Sheets

(51) Int. Cl.
  *A61F 13/494* (2006.01)
  *A61F 13/511* (2006.01)
  *A61F 13/15* (2006.01)
  *A61F 13/49* (2006.01)
  *A61L 15/24* (2006.01)

(52) U.S. Cl.
  CPC .... *A61F 13/49017* (2013.01); *A61F 13/4942* (2013.01); *A61F 13/51121* (2013.01); *A61L 15/24* (2013.01); *A61F 2013/15357* (2013.01); *A61F 2013/49093* (2013.01); *A61F 2013/51338* (2013.01)

(58) Field of Classification Search
  CPC ............ A61F 13/49017; A61F 13/4942; A61F 2013/49093; A61F 2013/51338; A61S 13/494
  See application file for complete search history.

(56) References Cited

U.S. PATENT DOCUMENTS

| | | | |
|---|---|---|---|
| 5,578,025 | A | 11/1996 | May |
| 5,993,433 | A * | 11/1999 | St. Louis ............ A61F 13/4942 604/385.27 |
| 9,993,369 | B2 * | 6/2018 | Xu ..................... A61F 13/15203 |
| 2001/3157859 | | 8/2003 | Ishikawa |
| 2003/0157859 | A1 | 8/2003 | Ishikawa |
| 2004/0005457 | A1 | 1/2004 | DeLuia et al. |
| 2004/0186454 | A1 | 9/2004 | Itoh et al. |
| 2005/0014428 | A1 | 1/2005 | Zenker et al. |
| 2009/0111347 | A1 | 4/2009 | Peng et al. |
| 2010/0286339 | A1 | 11/2010 | Autran et al. |
| 2012/0177886 | A1 | 7/2012 | Kanya et al. |
| 2012/0328850 | A1 | 12/2012 | Yahiaoui et al. |
| 2013/0239283 | A1 | 9/2013 | Yokoyama et al. |
| 2013/0325398 | A1 | 12/2013 | Nakagawa et al. |
| 2014/0000003 | A1 | 1/2014 | Ashraf et al. |
| 2014/0039434 | A1 | 2/2014 | Xu et al. |
| 2014/0088535 | A1 * | 3/2014 | Xu ..................... A61F 13/15203 604/366 |
| 2014/0127459 | A1 | 5/2014 | Xu et al. |
| 2014/0127461 | A1 | 5/2014 | Xu et al. |
| 2014/0284011 | A1 | 9/2014 | Krapsch et al. |
| 2014/0343523 | A1 * | 11/2014 | Viens .................... A61L 15/225 604/370 |
| 2015/0174282 | A1 | 6/2015 | Kanya et al. |
| 2015/0313766 | A1 * | 11/2015 | Miao ..................... A61F 13/475 604/385.101 |

FOREIGN PATENT DOCUMENTS

| | | |
|---|---|---|
| CN | 103108616 A | 5/2013 |
| CN | 107095747 A | 8/2017 |
| DE | 4432298 A1 | 3/1996 |
| EP | 1 035 818 A1 | 9/2000 |
| JP | 2000328420 A | 11/2000 |
| JP | 2003-521591 A | 7/2003 |
| JP | 2008289896 A | 12/2008 |
| JP | 2009001930 A | 1/2009 |
| JP | 2014194090 A | 10/2014 |
| MX | 2008015005 A | 2/2009 |
| WO | 96/01095 A1 | 1/1996 |
| WO | 98/24390 A | 6/1998 |
| WO | 9920215 A1 | 4/1999 |
| WO | 01/30289 A1 | 5/2001 |
| WO | 01/59193 A1 | 8/2001 |
| WO | 2004/029349 A1 | 4/2004 |
| WO | WO 2007/039828 A1 | 4/2007 |
| WO | 2007/140163 A2 | 12/2007 |
| WO | 2012/024576 A1 | 2/2012 |
| WO | WO 2012/024576 A1 | 2/2012 |
| WO | 2014/074409 A1 | 5/2014 |
| WO | 2014/074410 A1 | 5/2014 |
| WO | 2014098683 A1 | 6/2014 |

OTHER PUBLICATIONS

Extended European Search Report (Communication) dated Jul. 2, 2018, issued by the European Patent Office in corresponding European Application No. 15875793.0-1102. (8 pages).
Third Party Observations dated Jul. 17, 2018 by the Japanese Patent Office in Japanese Patent Application JP 2017-552779 (10 pages).
Office Action (Reason(s)) dated Jun. 29, 2018, by the Japanese Patent Office in corresponding Japanese Patent Application No. 2017-552779, and an English Translation of the Office Action. (11 pages).
Office Action (Decision of Rejection) dated Mar. 18, 2019, by the Japanese Patent Office in corresponding Japanese Patent Application No. 2017-552779, and an English Translation of the Office Action, 7 pages.
Office Action (Communication pursuant to Article 94(3) EPC) dated Mar. 27, 2019 by the European Patent Office in corresponding European Application No. 15 875 793.0-1102, 6 pages.
Office Action 1769, dated Apr. 29, 2019, by the Colombian Patent Office in Colombian Patent Application No. NC2017/0007859 and an English Translation of the Office Action. (21 pages).
Pre-Appeal Examination Report dated Aug. 9, 2019 by the Japanese Patent Office in Japanese Patent Application JP 2017-552779, 8 pages, with English Translation.
Third Party Observation dated Aug. 5, 2019 by the Japanese Patent Office in Japanese Patent Application JP JP2017-552779, 27 pages, with English Translation.
Office Action (Notice of Reasons for Rejection) dated Jan. 27, 2020, by the Japanese Patent Office in corresponding Japanese Patent Application No. 2017-552779, and an English Translation of the Office Action. (19 pages).
Office Action (Reason(s)) dated Sep. 28, 2020 by the Japanese Patent Office in corresponding Japanese Patent Application No. 2019-106075, and an English Translation of the Office Action. (18 pages).
Office Action (Text of the First Office Action) dated Nov. 5, 2019, by the China National Intellectual Property Administration in corresponding Chinese Patent Application No. 201580072181.1, and an English Translation of the Office Action. (18 pages).
Search Report dated Apr. 9, 2020, by the Brazilian Patent Office in corresponding Brazilian Patent Application No. BR112017011289-2, English Translation only, (4 pages).
International Search Report (PCT/ISA/210) dated Aug. 28, 2015, by the Swedish Patent Office as the International Searching Authority for International Application No. PCT/SE2015/000001.
Written Opinion (PCT/ISA/237) dated Aug. 28, 2015, by the Swedish Patent Office as the International Searching Authority for International Application No. PCT/SE2015/000001.
International Preliminary Report on Patentability (PCT/IPEA/409) dated Nov. 25, 2016, by the Swedish Patent Office as the International Searching Authority for International Application No. PCT/SE2015/000001.
Applicant's comments to Written Opinion in PCT/SE2015/000001, dated Oct. 27, 2016, 3 pages.
Collection of the "TSA Operating Instructions", Multi Functional Measuring System Tissue Softness Analyzer, Emtec Paper Testing Technology, Jul. 8, 2013, 53 pages.
DIPL.-PHYS. Giselher Grüner, "TSA—Tissue Softness Analyzer a new and objective measuring technique to anayze the softness of tissue", Emtec Paper Testing Technology, pp. 161-164.
Third Party Observation dated Jul. 13, 2018 by the Japanese Patent Office in Japanese Patent Application JP 2017-552779, 22 pages, English translation only.
Office Action (Reason(s)) dated Jun. 24, 2021 by the Columbian Patent Office in corresponding Columbian Patent Application No. NC2017/0007859, and an English Translation of the Office Action. (16 pages).

* cited by examiner

ABSORBENT ARTICLE HAVING A TOPSHEET AND STANDING GATHERS EACH HAVING A SHEET MATERIAL WITH SPECIFIED STIFFNESS, SOFTNESS AND SMOOTHNESS PROPERTIES

TECHNICAL FIELD

The present invention relates to an absorbent article, in particular a disposable absorbent article such as a disposable absorbent garment that may be in the form of a diaper or incontinence guard.

BACKGROUND

Infants and other individuals wear disposable absorbent articles, such as infant diapers and adult incontinent products to receive and contain body exudates or fluids such as urine. The absorbent articles are configured for single use and comprise an absorbent core or panel arranged between a liquid permeable topsheet and a liquid impermeable backsheet.

Current commercially available absorbent articles typically incorporate a pair of standing gathers, which extend upwardly generally about respective side edges of the absorbent core on the side of the topsheet. Such a standing gather defines a barrier or wall at the respective side edge of a central crotch area of the absorbent article, which acts to prevent or retard lateral flow of body fluidic material such as urine or fluidic fecal material.

The absorbent articles of the mentioned types should be comfortable during use, while being worn, and it is desired that the absorbent articles have a cloth-like and soft appearance as close to regular underwear as possible, while being easy to handle and grip by a hand of a user, e.g. when putting on and taking off the article.

There is still room for improvement with respect to comfort, fit and cloth-like feel of absorbent articles of the above-mentioned type.

SUMMARY

In view of the absorbent articles of the above-mentioned types, it is an object to provide an improved absorbent article that is comfortable and reliable to use, wherein the article is easy to handle and has a soft and cloth-like feeling, while being well-fitting to prevent any skin chafing and other sensory discomfort, as well as to prevent body fluid leakage from the absorbent article to the surrounding during use.

This object is wholly or partially achieved by an absorbent article according to appended claim 1. Embodiments are set forth in the appended dependent claims, in the following description and in the drawings.

Thus, there is provided an absorbent article having a wearer-facing side and a garment-facing side. The absorbent article extends in a longitudinal direction (L) and a transverse direction (T) and has a front end portion, a rear end portion and a crotch portion located intermediate the end portions. The absorbent article further comprises a topsheet arranged on the wearer-facing side, a backsheet arranged on the garment-facing side, an absorbent core enclosed between the topsheet and the backsheet, and a pair of standing gathers, which are arranged on the wearer-facing-side and extend substantially in the longitudinal direction (L).

The topsheet further comprises a sheet material having a stiffness (D) from 2.3 to 20 mm/N and each standing gather comprises a sheet material having a stiffness (D) from 2.0 to 20 mm/N, wherein stiffness is measured according to the softness test method as described herein. Furthermore, the topsheet sheet material has a softness (TS7) of 4.5 dB $V^2$ rms or less and the standing gather sheet material has a softness (TS7) of 5.0 dB $V^2$ rms or less, wherein softness is measured on a surface of each sheet material and according to the softness test method as described herein. The topsheet sheet material should also have a smoothness (TS750) of 4 dB $V^2$ rms or less and the standing gather (14,15) sheet material should have a smoothness (TS750) of 7.0 dB $V^2$ rms or less, wherein smoothness is measured on the surface of each sheet material and according to the softness test method as described herein.

The softness and smoothness are measured on the surface of each sheet material and each sheet material should present at least one surface that would result in the softness, smoothness and stiffness characteristics. The surface may be one forming part of an outer-facing surface of the absorbent article.

The term absorbent article refers to a product that is placed against the skin of the wearer to absorb and contain body exudates, like urine and faeces. The invention mainly refers to disposable absorbent articles, which are articles that are not intended to be laundered or otherwise restored or reused as an absorbent article after use. The absorbent article may be an incontinence pad, a sanitary pad or an absorbent garment such as a diaper and/or an incontinence guard that is intended be worn as a pant-type of absorbent article that may be in a belted or non-belted form for securing the garment around a wearer's waist as in known in the art.

The wearer-facing side of the absorbent article refers to the side facing the wearer during use and acts to receive body exudate and the garment-facing side refers to the side facing away from the wearer during use.

The term topsheet refers to a sheet or the like that forms the inner cover of the absorbent article and in use is placed in direct contact with the skin of the wearer. The topsheet may comprise a sheet material in the form of a fiber material such as a nonwoven material, e.g. spunbond, meltblown, carded, hydroentangled, wetlaid etc. Suitable fiber materials can be composed of natural fibers, such as wood pulp or cotton fibers, manmade fibers, such as polyester, polyethylene, polypropylene, viscose, nylon etc. or from a mixture of natural and manmade fibers. The nonwoven material may contain a high degree of polyolefin, in particular polypropylene or polyethylene. The nonwoven material may also contain a slip agent such as erucamide, a wax and a lubricant as further described herein. The topsheet material may further be composed of tow fibers, which may be bonded to each other in a bonding pattern, as e.g. disclosed in EP-A-1 035 818. Further examples of topsheet sheet materials are porous foams, apertured plastic films etc. The materials suited as topsheet materials should be soft and non-irritating to the skin and be readily penetrated by body fluid, e.g. urine. The topsheet may further be different in different parts of the absorbent article, e.g. comprise different topsheet materials as specified herein. The topsheet material that provides an absorbent article according to the present invention and that provides the characteristics in form of softness, smoothness and stiffness may be a sheet that forms a surface area of the total topsheet surface area that is larger than any one of the other sheet materials used in the topsheet forms. By surface is here meant a wearer-facing surface. The topsheet material of the invention may form a surface area of 30% or more, or 50% or more, of the total topsheet surface. The topsheet may also consist of the topsheet sheet material as specified herein. Sheet materials that are suitable for providing an absorbent article according to the present invention and provide the characteristics in form of softness, smoothness and stiffness properties may be provided by purposefully acting on compositional and/or process parameters as will be further described herein.

The backsheet forms the back cover of the absorbent article and will be discussed in more detail herein.

The standing gathers define barriers or walls at respective side edge portions of the crotch portion, which act to prevent or retard a lateral flow of body fluidic material such as urine or fluidic fecal material. The standing gathers may run substantially parallel to the longitudinal edges at the crotch portion in a longitudinal direction of the absorbent article. The standing gathers may contain elastics and may include an elastic material, such as an elastic thread, yarn or ribbon material, and may be elastically gathered at least in their centre portions, which provide means for a good fit so as to prevent any leakage.

Furthermore, at least one longitudinal elastic element may be arranged in the crotch portion at each side flap that may extend at a side outside each one of the standing gathers along the longitudinal direction (L) thereof. Each side flap may at least in part be made of the standing gather sheet material. Upon use of the absorbent article, the elastic elements may provide that the side flaps are elastically gathered and serve as leg elastic, which in turn provides an extra leakage barrier and a good fit to the wearer.

The standing gathers may comprise or consist of any of the materials described above for, for example, the topsheet. The standing gather may, for example, comprise or consist of a sheet material of nonwoven material, such as a spunbond material as further described herein. The nonwoven material may contain a high degree of polyolefin, in particular polypropylene or polyethylene. The nonwoven material may also contain a slip agent such as erucamide, a wax and a lubricant as further described herein. The sheet material of the standing gather may comprise two outer layers of a spunbond material and an intermediate layer between the outer layers that is of a meltblown material. Additional intermediate layers of spunbond or meltblown materials may also be provided. The standing gathers may further be different in different parts of the absorbent article, e.g. be of different standing gather sheet materials as specified herein. The standing gather sheet material that provides an absorbent article according to the present invention and that provides the characteristics in form of softness, smoothness and stiffness may be a sheet that forms a surface area of the total standing gather surface area that is larger than any one of the other sheet materials used in the standing gather forms. The standing gather material of the invention may form a surface area of 30% or more, or 50% or more, of the total sheet area of the standing gather. The standing gathers may also consist of the standing gather sheet material as specified herein. As mentioned above, the sheet materials that are suitable for providing an absorbent article according to the present invention that provide the characteristics in form of softness, smoothness and stiffness properties may be provided by purposefully acting on compositional and/or process parameters as will be further described in the hereinbelow.

An absorbent article with the combination of the specified topsheet and standing gather sheet materials is a well-fitting article presenting a soft and cloth-like feeling to the wearer. The combination of the soft and cloth-like materials aids in preventing any skin chafing as well as body fluid leakage from the absorbent article to the surrounding during wear of the absorbent article. The combination of soft portions in the article leads to a soft, cloth-like transition area between the two materials of the article, in turn providing the transition area with a sensorially invisible soft feeling against the skin of the wearer, wherein transition area between the soft materials is non-perceptible or hardly perceptible. In other words, a wearer of an article as disclosed herein, will perceive the inner skin-contacting surface of the article as being smooth and soft without any alternations or irregularities. Accordingly, the selected material combinations disclosed herein serve to conceal the standing gathers from being felt by the wearer as being element separate from the topsheet. The combination of these materials also provides for better elasticity of any elastics used in combination with the article, particularly within in the crotch portion and in the standing gathers and/or the side flaps, if present. The combined sheet materials may provide that less elastic material is required to provide sufficient elasticity to an elastic portion in the crotch portion of the absorbent article, which in turn leads to less risk of any skin chafing and body fluid leakage.

Thus, the topsheet may comprise the sheet material with a surface adjacent to or overlapping with the sheet material of a standing gather, which sheet materials provide similarly soft feeling, when worn by a wearer and which provide less irritation. In particular, as joints, seams and/or edges between the topsheet and the standing gather material may be scarcely noticeable by a wearer, they may cause less irritation and provide more comfort to the wearer.

The wearer will in fact appreciate standing gather elastic with more yield and flexibility as well as an improved fit of the absorbent article as compared to known articles, wherein the available elongation may be increased by the use of the combination soft materials so as to provide comfort to the wearer with less risk of chafing and body fluid leakage.

As indicated above, the sheet materials of the topsheet and of each standing gather may at least form parts of the topsheet and the standing gathers that overlap with the crotch portion of the absorbent article. The parts of the sheet material of the topsheet and of each standing gather may be arranged next to or in overlap with each other, at least when the absorbent article is worn by a wearer. This arrangement would indeed provide a soft, cloth-like transition area between the two materials of the article providing a sensorially invisible soft feeling against the skin of the wearer.

The sum of the stiffness of the topsheet sheet material and the stiffness of the standing gather sheet material may be 4.5 mm/N or more. The sum of the softness of topsheet sheet material and the softness of the standing gather sheet material may be 8.0 dB V^2 rms or less. The sum of the smoothness of the topsheet sheet material and the smoothness of the standing gather sheet material may be 8.0 dB V^2 rms or less.

The difference between the stiffness of the topsheet sheet material and the stiffness of the standing gather sheet material may be 0.5 mm/N or less. The difference between the smoothness of the topsheet sheet material and the smoothness of the standing gather sheet material may be 3.0 dB V^2 rms or less.

The backsheet may comprise a sheet material that has a stiffness (D) from 2.0 to 20 mm/N as measured according to the softness test method as described herein, The backsheet (12) sheet material may also have a softness (TS7) of 16 or less as measured on a surface of the backsheet sheet material and according to the softness test method as described herein.

The backsheet material should present at least one surface that would result in the softness, smoothness and stiffness characteristics. The softness and smoothness are preferably measured on a surface of each sheet that is intended to form part of an outer-facing surface of the absorbent article.

Thus, the absorbent article may in addition to the soft sheet materials of the topsheet and the standing gathers be arranged with the soft backsheet sheet material as specified by the stiffness, softness and smoothness values.

The backsheet forms the back cover of the absorbent article. The backsheet may be a liquid impermeable cover that may comprise a sheet material in the form of a thin plastic film, e.g. a polyethylene or polypropylene film, a nonwoven material coated with a liquid impervious material, a hydrophobic nonwoven material, which resists liquid penetration, or a laminate, e.g. of a plastic film and a nonwoven material. The outer liquid impermeable cover material may be breathable so as to allow vapor to escape from the absorbent core, while still preventing liquids from passing through. Examples of breathable outer liquid impermeable cover materials are porous polymeric films, nonwoven laminates from spunbond and meltblown layers, laminates from porous polymeric films, monolithic films with inherent breathability and nonwoven materials. The backsheet may also be different in different parts of the absorbent article. The backsheet material may at least in overlapping edges between each standing gather and the backsheet in the crotch portion comprise or consist of the soft backsheet material as specified herein. The backsheet material that provides an absorbent article according to the present invention and that provides the characteristics in form of softness and stiffness may be a sheet that forms a surface area of the total backsheet surface area that is larger than any one of the other sheet materials used in the backsheet forms. By surface is here meant a garment-facing surface. The backsheet material of the invention may form a surface area of 30% or more, or 50% or more, of the total sheet area of the backsheet. The backsheet may also consist of the backsheet sheet material as specified herein. As mentioned above, the sheet materials that are suitable for providing an absorbent article according to the present invention that provide the characteristics in form of softness, smoothness and stiffness properties may be provided by purposefully acting on compositional and/or process parameters as will be further described in hereinbelow.

An absorbent article with the combination of the specified backsheet, topsheet and standing gather sheet materials is a well-fitting article presenting a soft and cloth-like feeling to a wearer with all the advantages as described for the combination of the topsheet and standing gather sheet materials. In particular, the combination of the backsheet and standing gather sheet materials at side flaps within the crotch region may prevent any skin chafing as well as body fluid leakage from the absorbent article to the surrounding during wear of the absorbent article, wherein the soft sheet materials within an overlapping transition area of the side flaps are non-perceptible or hardly perceptible. The combination of all materials also provides for better elasticity of any elastics used in combination with the article, particularly within the crotch portion and in the standing gathers and/or the side flaps, if present. The combined sheet materials may require less elastic material in the side flaps and/or in the standing gathers to provide sufficient elasticity in an elastic portion of the absorbent article, which in turn leads to less risk of any skin chafing and body fluid leakage.

Thus, the backsheet may comprise the backsheet sheet material with a surface adjacent to or overlapping with the sheet material of a standing gather and then providing a soft feeling, when worn by a wearer. In particular, as joint, seam and/or edges between the backsheet and the standing gather material may be less noticeable by a user and may cause less irritation and provide more comfort to wear.

The wearer will in fact appreciate the leg elastic and standing gather elastic with more yield and flexibility as well as an improved fit of the absorbent article as compared to known articles, wherein the available elongation may be increased by the use of the combination soft materials so as to provide comfort to the wearer with less risk of chafing and body fluid leakage.

As indicated above, the sheet materials of the backsheet and of each standing gather may at least form parts of the backsheet and the standing gathers that overlap with the crotch portion of the absorbent article. The parts of the sheet materials of the backsheet and of each standing gather may be arranged next to or in overlap with each other. The parts may overlap at side flaps of the absorbent article.

The sum of the stiffness of the backsheet sheet material and the stiffness of the standing gather sheet material of may be 4.5 mm/N or more. The sum of the softness the backsheet sheet material and the softness of the standing gather sheet material may be 19 dB $V^2$ rms or less.

The difference between the stiffness of the sheet material of the backsheet and the stiffness of the standing gather sheet material may be 0.8 mm/N or less.

The sheet materials that are part of the topsheet and the standing gathers, and that may also be part of the backsheet, may be any one of the materials as, for example, described herein for use in such sheet materials for providing the absorbent articles that are soft with a cloth-like and sensorially invisible soft feeling against the skin of user wearing the absorbent article. Sheet materials that are suitable for use in an absorbent article according to the present invention can be provided in order to have the characteristics in form of softness, smoothness and stiffness properties by purposefully acting on compositional and/or process parameters, while other properties such as the tensile strength of the materials should remain acceptable for use in an absorbent article. For example, the polymer (-s) of the fibers in the nonwoven may be selected to provide the soft and smooth feeling, wherein a polyolefin such as polypropylene in fact provides a softer material than, for example, polyethylene terephthalate (PET). Furthermore, it may also be possible to act on the fiber thickness (preferably thin) and length of the fibers as well as the bonded area which preferably should be kept at minimum, and to act on modifying the bonding pattern (calendered bonding pattern with low percentage of bonding area) and other structures of the nonwoven influenced by, for example, embossment and ring-rolling procedures.

Additives such as slip agents and melt additives may also aid to provide a soft nonwoven material for use in the absorbent article. Plastic films such as the ones often used in a web material of backsheet laminate may also be acted on by modifying the basis weight, filler content for filled or breathable films, the stretching process and direction, the breathability and polymer composition by, for example, using different types of polyethylene types, such as a linear low-density polyethylene (LLDPE) and low-density polyethylene (LDPE), and/or polypropylene. Also the lamination of a film to another web material, such as a nonwoven web may also be acted on, e.g. by modifying the glue content, the glue application, the glue pattern and the amount of the glue. The laminate may also undergo one or more process steps of, for example, ring-rolling or embossing to make the laminate softer.

The backsheet material, standing gather sheet material and/or the topsheet material may, accordingly, comprise a nonwoven material of fibres. The nonwoven material may comprise polyolefin-containing fibres, such as polypropylene-containing fibres. The polyolefin, such as polypropylene, may be present in an amount of 50% by weight or more, or 75% by weight or more. The fibres may contain a slip agent, such as a polyolefin wax, primary and secondary amides such as erucamide and oleamide, and stearyl derivatives. The slip agent may be present in an amount of 0.1 to 5% by weight. The polyolefin-containing fibres may comprise polyethylene. The fibres may contain polyethylene in an amount of from 5 to 40% by weight. The polyolefin-containing fibres may be bicomponent fibres, e.g. with a core of polypropylene and an outer shell of polyethylene.

The nonwoven material may comprise a layer of a nonwoven (nonwoven web) with a first side surface and a second side surface, both extending in a plane that is parallel to a main plane of the material, wherein the polyolefin fibres may be bound together by an alternating bonding pattern that may have a total bonded surface area of from 5 to 30% of the total surface area of the first side surface.

The nonwoven material may comprise a layer of spunbond material, which in turn may also be the web having the bonding pattern. The nonwoven material may also comprise a layer of meltblown material. The nonwoven may then comprise two outer layers of a spunbond material and an intermediate layer between the outer layers that is of a meltblown material forming, for example a spunbond-meltblown-spunbond (SMS) material. Additional spunbond and meltblown layers may also be part of the nonwoven material.

The invention will now be described in more detail with reference to embodiments and drawings.

DETAILED DESCRIPTION

The present invention relates to an absorbent article such as absorbent garments in the form of infant diapers and adult incontinent products to receive and contain body exudates or fluids such as urine. The absorbent articles are configured for single use and comprise an absorbent core or panel arranged between a liquid permeable topsheet and a liquid impermeable backsheet.

In the following, the absorbent article will be exemplified by an absorbent garment in the form of a diaper.

Figure 1:
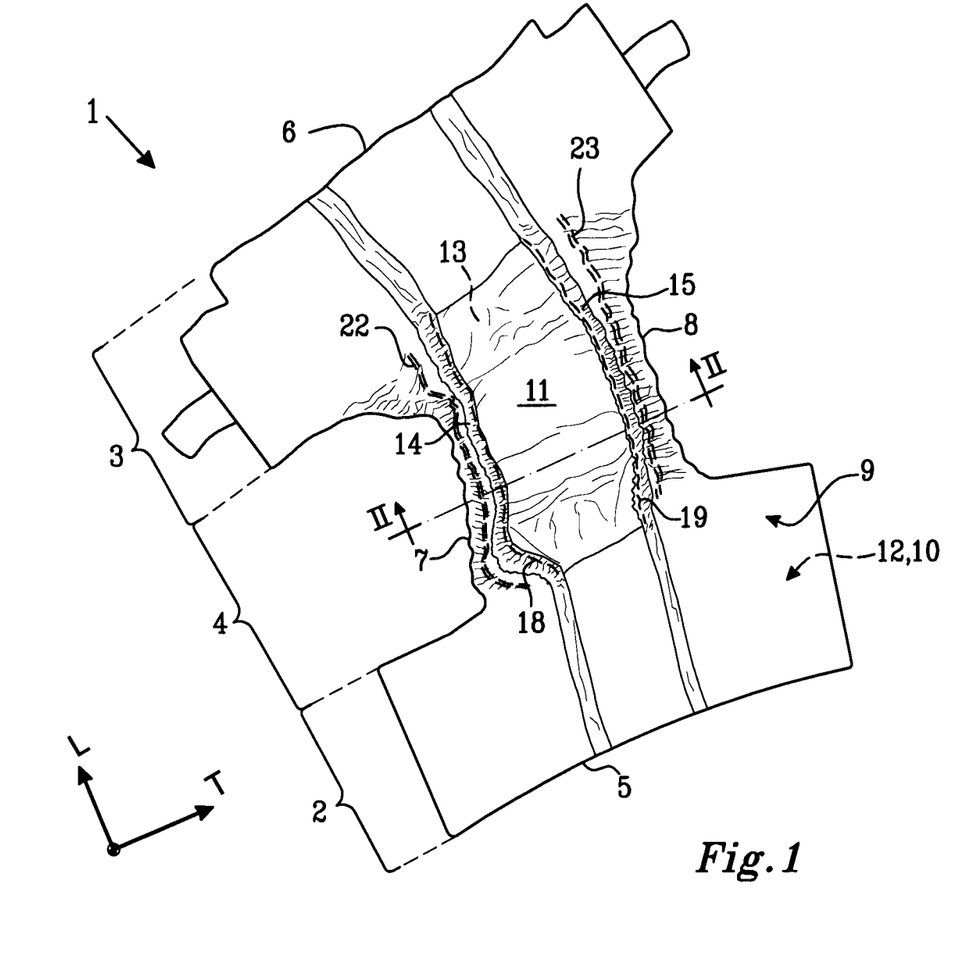
FIG. 1 illustrates an embodiment of an absorbent article in the form a diaper, which may be arranged with the soft materials according to the invention.

FIG. 1 illustrates such an absorbent article 1 in the form of a diaper 1.

The diaper 1 has a longitudinal direction L and a transverse direction T, and a front end portion 2, a rear end portion 3 and a crotch portion 4 located intermediate the end portions 2,3. The end portions 2,3 are placed on either side of the crotch portion 4 in the longitudinal direction L of the diaper 1 and are meant to be placed towards the front and to the rear of a wearer. The crotch portion 4 is the portion of an absorbent article 1 which is intended to be placed against the crotch of a wearer during wearing of the absorbent article 1 and to constitute the main acquisition area for body fluid that reaches the absorbent article 1. Front and rear end edges 5, 6 extend in the transverse direction T and side edges 7,8 extend generally in the longitudinally direction L, from the front portion 2 to the rear portion 3.

The diaper 1 has two faces 9,10, one of which faces the wearer during use and acts to receive body exudate, referred to herein as a wearer-facing side 9, and the other of which faces away from the wearer during use, referred to herein as a garment-facing side 10. The garment-facing side 10 is intended to face the wearer's clothes. The diaper 1 comprises a topsheet 11 arranged on the wearer-facing side 9, a backsheet 12 arranged at the garment-facing side 10. An absorbent core 13 is enclosed between the topsheet 11 and the backsheet 12.

The topsheet 11 refers to a sheet or the like that forms the inner cover of the diaper 1 and which in use is placed in direct contact with the skin of the wearer. The topsheet 11 may comprise a sheet material which may be any one of the materials described herein for use in a topsheet 11 for providing a soft and cloth-like feeling, which in turn may provide combined softness properties with other materials of the diaper 1 as further explained herein to provide combined softness and smoothness in transitional areas between materials that are arranged next to each other for a sensorially invisible soft feeling against the skin of user wearing the diaper 1. The sheet material may, for example, be a nonwoven material, such as a spun-bond material as further described herein. The nonwoven material may contain a high degree of polyolefin, in particular polypropylene and/or polyethylene. The nonwoven material may also contain a slip agent such as erucamide, a polyolefin wax and/or a lubricant as further described herein.

The backsheet 12 forms the back cover of the diaper 1. The backsheet 12 may comprise a sheet material that may be any one of the materials described herein above for use in a backsheet 12 for providing an outer cover or portion thereof that is soft with a cloth-like feeling, which material in turn may provide combined softness and smoothness properties with other materials of the diaper 1 as further explained herein to provide combined softness between materials that are arranged next to each other. The sheet material may, for example, comprise a nonwoven material comprising polyolefin fibers such as polyethylene and/or polypropylene fibers as further described herein.

A pair of longitudinal leakage barriers in the form of standing gathers 14,15 is arranged on the wearer-facing side 9 about respective side edges of the absorbent core at the sides 16,17 of the topsheet 11. The standing gathers 14,15 define barriers or walls at respective side edge portions of the crotch portion 4, which act to prevent or retard a lateral flow of body fluidic material such as urine or fluidic fecal material. The standing gathers 14,15 run substantially parallel to the longitudinal edges 21 at the crotch portion 4 in a longitudinal direction L of the diaper, which can be seen in FIG. 1. The standing gathers 14,15 contain elastics 18,19 and are elastically gathered at least in their centre portions, which provide means for a good fit so as to prevent any leakage.

Side flaps 20,21 extend at the sides outside the standing gathers 14,15 and each side flap 20,201 possesses at least one longitudinal elastic element 22a-b; 23a-b in the crotch portion 4 along the longitudinal direction L thereof. Upon use of the diaper, the elastic elements 22a-b; 23a-b provide that the side flaps 20,21 are elastically gathered and serve as leg elastic, which in turn provides an extra leakage barrier and a good fit to the wearer.

As illustrated in the figures, the standing gathers 14,15 extend in the longitudinal direction L over the entire length of the diaper. It will be appreciated, however, that, depending on production techniques employed, the standing gathers 14,15 may terminate short of the transverse edges 5,6 of the diaper. As is most readily apparent from FIG. 2, each standing-gather 14,15 has a free-standing first end edge region 24,25 and a second end edge region 26,27 attached at least to the backsheet 12 and/or topsheet 12. The free-standing first end edge region 24,25 extends freely from the proximal end 28,29 thereof. At the crotch region 4, the proximal end 28,29 is in this case located transversally inwardly of the side flaps 20,21 and the leg elastic material 22$a$-$b$;23$a$-$b$.

Figure 2:
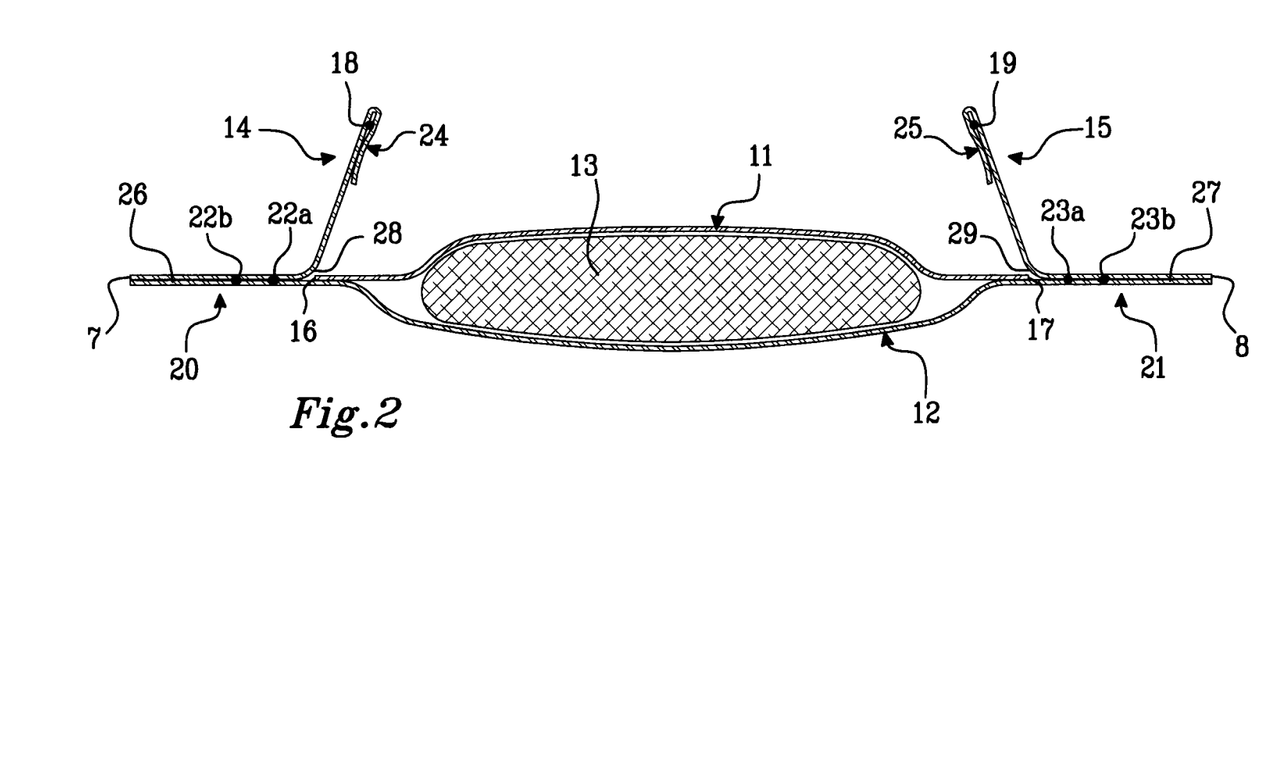
FIG. 2 is a transversal cross-sectional side view of a first embodiment of the absorbent article as shown in FIG. 1 taken along the line II-II.

The elastics 18,19 of each standing gather 14,15 may as illustrated in the figures be arranged in the free-standing first end edge region 24,25 within a first pocket which, in a conventional manner, accommodates a thread 18,19, yarn or ribbon of elastic material extending in the longitudinal direction L. The second end edge region 26,27 together with the backsheet to which it is attached at the crotch region delimits leg elastic channels for each leg elastic material 22$a$-$b$;23$ab$. The leg elastic material may also be a thread 22$a$-$b$;23$a$-$b$, yarn or ribbon of elastic material extending in the longitudinal direction L. One or more threads, yarns or ribbons may be used to form elastic in each standing gather 14,15 and in the leg elastic.

As illustrated in FIG. 2, the topsheet 11 may at least in the crotch region 4, be arranged in a region delimited by the standing gathers 14,15. It will be appreciated, however, that, depending on production techniques employed, the topsheet 11 may transversally extend in between the backsheet 12 and the standing gathers 14,15, thereby forming part of the side flaps 20,21 (not shown). The standing gathers 14,15 may alternatively terminate short to the proximal ends 28,29 of the standing gathers 14,15 as is known in the field, and not transversally extend all the away to the side edges 7,8 as shown in FIG. 1.

The standing gathers 14,15 may comprise or consist of any of the materials described above for, for example, the topsheet. The standing gather may, for example, comprise or consist of a sheet material of nonwoven material, such as a spun-bond material as further described herein. The nonwoven material may contain a high degree of polyolefin, in particular polypropylene or polyethylene. The nonwoven material may also contain a slip agent such as erucamide, a polyolefin wax and/or a lubricant as further described herein. The sheet material of the standing gather 14,15 may comprise two outer layers of a spunbond material and an intermediate layer between the outer layers that is of a meltblown material. Additional intermediate layers of spunbond or meltblown materials may also be provided.

The absorbent core 13 is the absorbent structure disposed between the topsheet 11 and backsheet 12 of the diaper 1 in at least the crotch portion 14 thereof. The absorbent core 13 may be made up of any suitable absorbent or fluid uptake material as known in the art, such as one or more layers of cellulose fluff pulp, foam, fiber waddings, etc. The absorbent core 13 may contain fibers or particles of highly absorbent polymer material, commonly known as superabsorbents, which are materials having the ability to absorb and retain large quantities of fluid upon formation of a hydrogel. Superabsorbent polymers are water-swellable, water-insoluble organic or inorganic materials capable of absorbing at least about 20 times its weight of an aqueous solution containing 0.9 weight percent of sodium chloride. The superabsorbents may be mixed with cellulose fluff pulp and/or may be arranged in pockets or layers in the absorbent core 13. The absorbent core 13 may further incorporate components for improving the properties of the absorbent core 13. Some examples of such components are binder fibers, fluid-dispersing materials, fluid acquisition materials, etc. as known in the art.

The diaper 1 may comprise more than one absorbent core 13. The cores may, for example, be an upper large core and a lower, small core. The reverse arrangement with a smaller upper core and a large lower core is also known in the art.

The sheet materials that are part of the topsheet 11 and the standing gathers 14,15, and that may also be part of the backsheet 12 may be any one of the materials described herein for use in such sheet materials for providing absorbent articles that are soft with a cloth-like feeling and a sensorially invisible soft feeling against the skin of user wearing the absorbent article 1. The sheet materials should have the stiffness, softness and smoothness properties according to the present invention. The sheet materials that are suitable for use in an absorbent article 1 according to the present invention can be provided by purposefully acting on compositional and/or process parameters, while other properties such as tensile strength of the materials should remain acceptable for use in the absorbent article 1. For example, the polymer (-s) of the fibers in the nonwoven may be selected to provide the soft and smooth feeling, wherein a polyolefin such as polypropylene may provide a softer material than, for example, polyethylene terephthalate (PET). Furthermore, it may also be possible to act on the fiber thickness (preferably thin) and length of the fibers as well as the bonded area, which preferably should be kept at a minimum. The skilled person may also act on modifying the bonding pattern (calendered bonding pattern with low percentage of bonding area) and other structures of the nonwoven influenced by, for example, embossment and ring-rolling procedures.

Additives such as slip agents and melt additives may also aid to provide a soft nonwoven material for use in the absorbent article 1. Plastic films such as the ones often used as a web material (layer) of a backsheet 2 laminate may also be acted on by modifying the basis weight, filler content for filled or breathable films, stretching process and direction, breathability and polymer composition by, for example, using different types of polyethylene types, such as LLDPE and LDPE, and/or polypropylene. Also the lamination of a film to another web material, such as a nonwoven material may be acted on, e.g. by modifying the glue content, the glue application and pattern and the amount of the glue. The laminate may also undergo one or more additional process steps, such as ring-rolling, embossing or micro-perforated for breathability to make the laminate softer.

The backsheet 12 sheet material, standing gather 14,15 sheet material and/or the topsheet 11 sheet material may accordingly comprise a nonwoven material of fibres. The nonwoven material may comprise polyolefin-containing fibres, such as polypropylene-containing fibres. The polyolefin, such as the polypropylene, may be present in an amount of 50% by weight or more, or 75% by weight or more. The fibres may contain a slip agent, such as a polyolefin wax and primary and secondary amides, such as for instance erucamide and oleamide, and stearyl derivatives. The slip agent may be present in an amount of 0.1 to 5% by weight. The fibres may suitably have a tex of less than 2.5 dtex. A tex is metric measure of the weight per unit of a fibre. It is numerically equal to the weight in grams of ten kilometres (1000 meters) of the fibre. The fibres may have a fibre diameter of 0.5-100 μm, wherein spunbond fibres are usually in the range of 10-100 µm meltblown fibres are usually in a lower range of 0.5-10 µm. The melt flow rate (MFR) of a polypropylene material to be used in the fibres is suitably less than 90 dg/min as determined using ASTM test method D1238, 2.16 kg.

The nonwoven material may comprise a layer of a nonwoven (nonwoven web) with a first surface and a second surface, both extending in plane that is parallel to a main plane of the material, wherein the polyolefin fibres may be bound together by an alternating bonding pattern that may have a total bonded surface area of from 5 to 30% of the total surface area of the first surface. A combination of an alternating pattern of bonded and non-bonded areas, polyolefin-containing fibres such as polypropylene-containing fibres and a high surface of the non-bonded area may provide high softness, in particular if the fibres in addition contain a slip agent.

The nonwoven material may comprise a layer of spunbond material, which in turn may also be the web having the bonding pattern. The nonwoven material may also comprise a layer of meltblown material. The nonwoven may then comprise two outer layers of a spunbond material and an intermediate layer between the outer layers that is of a meltblown material forming, for example a spunbond-meltblown-spunbond (SMS) material. Additional spunbond and meltblown layers may also be part of the material.

The polyolefin-containing fibres may comprise polyethylene. The fibres may contain polyethylene in an amount of 5 to 40% by weight. The polyolefin-containing fibres may be bicomponent fibres, preferably with a core of polypropylene and an outer shell of polyethylene.

As is appreciated, the sheet materials of the invention may contain one or more layers of materials, such as the nonwoven material. A single nonwoven layer may then have a basis weight in the range of 5-30 g/m2 and each sheet material formed thereof may have a basis weight in the range of 5-80 g/m2.

The specific bonding pattern may also be selected so as to provide a soft and strong sheet material. The bonding pattern of the nonwoven material may adopt a diamond pattern as, for example, described in WO 2012/024576. For example, a backsheet material may comprise a nonwoven material having such diamond pattern and being laminated to film in accordance with the process described in WO 2007/039828.

The bonding pattern may also be provided by providing the nonwoven material in the form of a web with an alternating pattern of non-bonded areas and bonded areas, the bonded areas being in the form of rods which are extending in the cross machine direction (CD) of the web. The cross machine direction is the direction along the web material substantially perpendicular to the direction of forward travel of the web material through the manufacturing line in which the web material is manufactured. The rods may be provided by subjecting the web to a calender nip between rolls of which one contains a pattern forming the rod bonds.

Thus, the nonwoven material may form a nonwoven web of the sheet material of standing gather, topsheet and/or back sheet. Such a nonwoven material may comprise a plurality of polypropylene-containing fibers that in addition in fibers may contain a slip agent. The web may have a side which is provided with an alternating pattern of individualized bonded areas which bonded areas are in the form of rods which are arranged in the cross direction of the web, the alternating pattern of individualized bonded areas defines a non-bonded area. The surface of the bonded areas may be in the range of 5-30% of the total surface of the side, and the surface of the non-bonded area may be in the range of 70-95% of the total surface of the side. Such a material may be soft and strong.

As the skilled person will appreciate, many embodiments and alternatives are possible within the scope of the present application. For example, an aspect may be an absorbent article arranged with the sheet materials of the backsheet and the standing gather that have the stiffness, softness and smoothness properties according to the appended claims, with the option only of having a topsheet material with the stiffness, softness and smoothness properties according to the appended claims. The arrangement of the sheet materials and the material contents may all be as described herein.

EXAMPLES AND DESCRIPTION OF TEST METHODS

Sheet materials for use in the absorbent article according to the invention were investigated for properties of softness, smoothness and stiffness. It has been found that these properties as measured in the softness test method as described hereinbelow may be used for testing whether or not an absorbent article provides a material that fulfils the requirements of softness, comfort and reliability in use.

Furthermore, absorbent articles comprising the soft materials were tested for available elongation of the elastic standing gathers as well as the side flaps with leg elastics, wherein a good available elongation indicates that an absorbent article would provide a good yield and flexibility at elastic portions, which in combination with soft materials contributes to providing comfort and good fit to a wearer with less risk of chafing and body fluid leakage.

Softness Test Method—TSA Method

Softness, smoothness and stiffness properties of different sheet materials may be analysed with a softness test method (TSA method—Tissue Softness Analyzer method), a method that uses acoustic waves and has demonstrated to correlate well with hand panel tests for thin materials like tissue or nonwoven. The softness test method has therefore been used for determining suitable softness, smoothness and stiffness of a sheet material such as the topsheet, backsheet and standing gather sheet materials as described herein.

The test method follows the general outline of the TSA instrument manual dated 2013 Jul. 8 (Multi Functional Measuring System, Tissue Softness Analyzer) that is available from EMTEC electronic GMBH (Gorkistrasse 31; D-04347 Leipzig Germany) with the settings or modifications as set forth therein or below.

Technical Basics of TSA

The hand feel of a fibrous material is affected by components at various levels; from the polymers at a molecular level to the fibrous network at a macro level. Stiffness of individual fibres, internal structure, fibre-to-fibre bond strength, softener chemicals etc. all affect the hand feel, but so do also a mechanical treatment of the web material such as creping, and embossing. Because of its principle, the TSA analysis can measure effects of material differences at various levels.

Measuring Principle

The sample will be fixed in a measuring cell like a drumhead. Below is placed a vibration sensor, above is placed a vertical movable measuring head with a rotating blade that will be pushed onto the sample with a defined load. In step 1 of the procedure, a rotation with defined speed will be executed. The motion of the blades over the sample generates different types of vibrations/noise, which will be detected with a vibration sensor. In step 2 of the procedure, the sample will be deformed perpendicular to the surface to measure elastic, visco-elastic and plastic properties.

Evaluation

The resulting vibrations/noise spectrum from step 1 of the measurement is an overlapping of two single spectra; (a) Vertical vibration of the sample like a membrane and (b) Excitation of horizontal vibrations of the blades itself caused by momentary blocking and swinging back of the blades by the fibres, when moving over the surface.

In step 2 of the measurement the rotor applies a defined load in three cycles in vertical direction onto the sample, the load (F) being 0 mN, 100 mN and constant of 600 mN.

Reference is made to the Emtec manual for further details of the measuring principle. The measured deformation D correlates with the stiffness of the material.

Thus, the method results in three parameters, namely TS7—softness, TS750—smoothness and D—stiffness, which all are of relevance for evaluating whether an article may possess a soft and cloth-like feeling to a wearer. A high value of D and low values of TS7 and TS750 have shown to correspond to the provision of a desired soft material as touched upon by a hand a person.

Apparatus, Materials and Conditions

As mentioned above, the test follows the general outline of the TSA instrument manual dated 2013 Jul. 8 (Multi Functional Measuring System, Tissue Softness Analyzer) that is available from EMTEC electronic GMBH (Gorkistrasse 31; D-04347 Leipzig Germany) with the settings or modifications as set forth therein or herein.

A Tissue Soft Analyzer (TSA) from EMTEC electronic GMBH (TSA Tissue Softness Analyzer, model B458; UC version 1.72, Serie no.: 16.02.04.14.32; Software: emtec 3.18 13-ems-143; Hard Ware: 2.4 and Windows 7 Enterprise Service pack 1) was used in the measurements according to the method.

Samples were taken from sheet materials before they should have been assembled together with other materials to form an absorbent article. The Sample diameter of each sheet material sample was 112.8 mm and the tested diameter was about 70 mm, wherein the standard rotor (about 59 mm in diameter) of the instrument was used at a rotation speed of 2 rps.

The Softness resonance frequency peak of the measurements was 6.500 Hz.

The TS7 (softness) and TS750 (smoothness) values measured by the TSA instrument were controlled by using two standard Emtec reference and verification samples (Ref 2 TS and Ref 2.4 TS).

All measurements and calibrations were performed at standard climatic conditions of 23° C. (±1° C.) and 50% r.H. (±5%) in general following ISO DIN EN 20187.

The TSA is equipped with a balance for determination of grammage and thickness (gravimetric) of the samples in accordance with ISO 12625-6:2005.

Example—Softness Test Method

Backsheet Sheet Material—Samples and Results

A backsheet sheet material for use in an absorbent article according to the appended claims was tested in the softness test method. The sheet material contained a nonwoven web of bicomponent fibres of 1.0-2.0 denier containing 70% by weight of polypropylene in the core and an outer sheet of 30% by weight of polyethylene. The web had a basis weight of 18 g/m². The nonwoven material was made with 25% bonding surface area and in a diamond bonding pattern as for example described in WO 2012/024576. The nonwoven was laminated to film using 1 g/m² of glue in accordance with the process described in WO 2007/039828, the film being a breathable polyethylene film of 15 g/m² that was formed as described in WO 2007/039828. The final sheet material had a basis weight of 34 g/m².

As a comparison, a reference material (CAL C29H available from Clopay Europe) was tested. This sheet of material has been fabricated from PE film that was filled with $CaCO_3$ and stretched to be breathable (15 gsm), and which was laminated to a standard PP nonwoven (12 gsm) by using glue (2 gsm).

TABLE 1

Backsheet sheet material properties

|  | Reference material | Soft material |
|---|---|---|
| Producer | Clopay Europe | Polimira |
| Product number or name | CAL C29H | Mira velo bico |
| Basis weight, gsm | 29 | 34 |
| Softness, TS7 [dB V^2 rms] | 18.79 | 15.15 |
| Stiffness D [mm/N] | 1.75 | 2.06 |

The result as set forth in Table 1 indicates that the soft sheet material of the backsheet indeed is presenting a lower softness value and a higher stiffness than the reference material, thus forming a soft sheet material with proper stiffness for use in an absorbent article of the invention. This has also been confirmed by forming a diaper of the soft sheet materials as tested herein. A person in contact with the soft material also considered it softer than the reference material.

Topsheet Sheet Material—Samples and Results

Two topsheet sheet materials for use in an absorbent article according to the appended claims were tested in the softness test method. Each sheet material was a spunbond-containing material of fibres with bonded areas in form of circular rods in in the cross-machine direction (CD) using a melt additive. The soft spunbond material #2 contained polypropylene (MFR 25; LyondellBasell Moplen HP462R; CAS Registry #9003-07-0; 95% by weight), whitener (Ampacet White 41088; 1% by weight), a slip agent (Clariant Cesa-Slip PP 42161; Material Number: PPA0050079; 3% by weight) and topical treatment (chill & Seilacher Silastol PHP26; 1% by weight). The soft sheet material #1 had a similar content.

As a comparison, a reference material (SS5FW-01 016DS/016DU, FITESA, Sweden) was tested.

TABLE 2

Topsheet sheet material properties

|  | Reference material | Soft material #1 | Soft material #2 |
|---|---|---|---|
| Producer | Fitesa | Fitesa | Fitesa |
| Product code | SS5FW-01 016DS/016DU | SS4KW-30 020CH | SS4KW-30 016DU |
| Basis weight, gsm | 16 | 20 | 16 |
| Softness, TS7 [dB V^2 rms] | 4.99/4.68* | 5.11/2.91* | 3.07/4.42* |
| Smoothness, TS750 [dB V^2 rms] | 4.45/4.91* | 2.96/2.98* | 2.22/2.36* |
| Stiffness D [mm/N] | 2.07/2.09* | 2.44/2.47* | 2.73/2.72* |

*The two values for each property and sample represents measurements made on two outer surfaces of the sheet material, wherein the rotor or load is applied on each opposite surface providing two values (Y/X).

The result as set forth in Table 2 indicates that the soft material of the topsheet sheet material indeed has lower softness and smoothness values and higher stiffness than the reference material, thus forming a soft sheet material with proper stiffness for use in an absorbent article of the invention. This has also been confirmed by forming a diaper of the soft sheet materials as tested herein. A person in contact with the soft material also considered it softer than the reference material.

Standing Gather Sheet Material—Samples and Results

A standing gather sheet material for use in an absorbent article according to the appended claims was tested in the softness test method. The sheet material was a nonwoven material of fibres with bonded areas in form of circular rods in in the cross-machine direction (CD) using a melt additive. The nonwoven material was in the form of a spunbond-meltblown-spunbond (SMS). The soft material contained polypropylene (MFR 25; CAS Registry #9003-07-0; 76% by weight); polypropylene (MFR 800; CAS Registry #9003-07-0; 20% by weight), Whitener (TiO2 1% by weight) and a Slip agent (Erucamide; 3% by weight).

As a comparison, a reference material (H0101502/H20101500/H50101500, Fibertex) was tested.

TABLE 3

Standing gather sheet material properties

| | Reference material | Soft material |
|---|---|---|
| Producer | Fibertex | Fitesa |
| Product code | H0101502/H20101500/H50101500 | SS6KW-30 015NN |
| Basis weight, gsm | 15 | 15 |
| Softness, TS7 [dB V^2 rms] | 5.81/8.1* | 4.84/3.01* |
| Smoothness, TS750 [dB V^2 rms] | 10.07/10.71* | 6.53/4.36* |
| Stiffness D [mm/N] | 1.84/1.84* | 2.19/2.23* |

*The two values for each property and sample represents measurements made on two outer surfaces of the sheet material, wherein the rotor or load is applied on each opposite surface providing two values (Y/X).

The result as set forth in Table 3 indicates that the soft material of the topsheet sheet material indeed has lower softness and smoothness values and higher stiffness than the reference material, thus forming a soft sheet material with proper stiffness for use in an absorbent article of the invention. This has also been confirmed by forming a diaper of the soft sheet materials as tested herein. A person in contact with the soft material also considered it softer than the reference material.

Available Elongation

The elastic properties as available elongation are measured on a well-defined test piece that is cycled in a tensile tester from unstretched position to full length. The available elongation (Tt) is defined as the elongation of the sample when it is stretched from unaffected and contracted state to full length and it is calculated and expressed in percent of the length of the unaffected sample.

A good available elongation in the standing gather as well as the side flaps (leg elastic) is beneficial for a number of reasons, e.g. absorbent articles comprising the soft materials having a good available elongation would provide a good yield and flexibility at elastic portions so as to provide comfort to a wearer with less risk of chafing and body fluid leakage.

The standing gather and the side flaps were removed from each sample diaper with a pair of scissors. A specified length of each sample material (e.g. 50 mm) was then inserted between the jaws of a tensile tester (available e.g. from the Lloyd or Instron corporations). The sample should be inserted without slack, but still without significant tension. The sample is then extended in three cycles, with a cross-head speed of 500 mm/min. The end point is identical over the three cycles, and should be set to a point where the sample is fully stretched or extended, but without the materials being overstretched. This point can be determined e.g. in a separate tensile test (where the stress versus strain curve turns sharply upwards, and where material folds and wrinkles are straightened out), or by hanging stepwise increasing weights in the standing gather strip to the same effect. The available elongation (in percent) is read from data from the third cycle, according to the formula:

$$\text{Available elongation (\%)} = \frac{100 * (L - L_0)}{L_0}$$

wherein:
L=the sample length when fully extended
L0=the initial clamping length (e.g. 50 mm) plus the length of the permanent deformation. This latter length is taken on the strain axis in the stress/strain graph on the (third) return cycle, from the zero point to the point where the force goes below 0.1 N.

Example—Available Elongation

A comparative test was made between reference samples taken from conventional absorbent articles (produced by SCA Hygiene AB) and sample taken from "soft" absorbent articles. The conventional absorbent articles had sheet materials that have similar softness, smoothness and stiffness properties as the reference sheet materials that were tested in the softness test method above. The soft absorbent articles had the soft sheet materials of the invention corresponding to the ones that were tested in the softness test method above. The constructions of the standing gather and the side flaps of the tested absorbent articles were held equal in all other respects.

TABLE 4

Available Elongation (%) 0.1N - Standing Gather (SG)

| | Available Elongation (%) | | | |
|---|---|---|---|---|
| Sample | Mean | StDev | Minimum | Maximum |
| Reference sample (Left)* | 118.59 | 1.60 | 116.41 | 120.79 |
| Reference sample (Right)** | 107.48 | 2.26 | 104.89 | 110.31 |
| "Soft" sample (Left)* | 129.32 | 2.30 | 125.41 | 131.37 |
| "Soft" sample (Right) ** | 126.12 | 1.86 | 124.64 | 129.26 |

TABLE 5

Available Elongation (%) 0.1N - Side flap/Leg Elastic (LE)

| | Available Elongation (%) | | | |
|---|---|---|---|---|
| Sample | Mean | StDev | Minimum | Maximum |
| Reference sample (Left)* | 78.46 | 8.45 | 67.27 | 87.03 |
| Reference sample (Right)** | 88.85 | 4.49 | 82.49 | 94.59 |
| "Soft" sample (Left)* | 103.34 | 2.02 | 101.18 | 105.36 |
| "Soft" sample (Right)** | 110.26 | 2.09 | 107.63 | 112.43 |

*Left means that the sample was taken from the left side of the absorbent article as viewed from the rear portion to the front portion.

**Right means that the sample was taken from the right side of the absorbent article as viewed from the rear portion to the front portion.

From the result as set forth in Tables 4 and 5, it is made clear that the change from conventional sheet materials to soft nonwoven sheet materials had a significant effect on the measured available elongation.

The invention claimed is:

1. An absorbent article having a wearer-facing side and a garment-facing side, the absorbent article extending a longitudinal direction and a transverse direction and having a front end portion, a rear end portion and a crotch portion located intermediate the end portions, wherein the absorbent article comprises a topsheet arranged on the wearer-facing side, a backsheet arranged on the garment-facing side, an absorbent core enclosed between the topsheet and the backsheet, and a pair of standing gathers, which are arranged on the wearer-facing-side and extend substantially in the longitudinal direction, the topsheet comprising a sheet material comprising a nonwoven material comprising polypropylene-containing fibers and each of the standing gathers comprising a sheet material comprising a nonwoven material comprising polypropylene-containing fibers,
wherein the topsheet sheet material has a stiffness from 2.3 to 20 mm/N and each standing gather sheet material has a stiffness from 2.0 to 20 mm/N, wherein stiffness is measured according to a softness test method, wherein the softness test method is TSA method—Tissue Softness Analyzer method,
wherein the topsheet sheet material has a softness of 4.5 dB V^2 rms or less and the standing gather sheet material has a softness of 5.0 dB V^2 rms or less, wherein softness is measured on a surface of each sheet material and according to the softness test method,
wherein the topsheet sheet material has a smoothness of 4 dB V^2 rms or less and the standing gather sheet material has a smoothness of 7.0 dB V^2 rms or less, wherein smoothness is measured on the surface of each sheet material and according to the softness test method,
wherein the polypropylene-containing fibers of the topsheet sheet material and the polypropylene-containing fibers of each of the standing gathers sheet material contain a slip agent, and
wherein the nonwoven material of the topsheet sheet material and the nonwoven material of each of the standing gather sheet material comprises a side surface, wherein the polypropylene-containing fibres of each of the nonwoven materials are bound together by an alternating bonding pattern of individualized bonded areas which are in the form of rods which are arranged in the cross direction of the web, the alternating pattern of the individualized bonded areas defining a non-bonded area, the surface of the bonded surface area being from 5 to 30% of the total surface area of the side surface, and the surface of the non-bonded area being from 70 to 95% of the total surface area of the side surface of each of the nonwoven materials.

2. The absorbent article according to claim 1, wherein the sum of the stiffness of the topsheet sheet material and the stiffness of the standing gather sheet material is 4.5 mm/N or more.

3. The absorbent article according to claim 1, wherein the sum of the softness of topsheet sheet material and the softness of the standing gather sheet material is 8.0 dB V^2 rms or less.

4. The absorbent article according to claim 1, wherein the sum of the smoothness of the topsheet sheet material and the smoothness of the standing gather sheet material is 8.0 dB V^2 rms or less.

5. The absorbent article according to claim 1, wherein the difference between the stiffness of the topsheet sheet material and the stiffness of the standing gather sheet material is 0.5 mm/N or less.

6. The absorbent article according to claim 1, wherein the sheet materials of the topsheet and of each standing gather at least form parts of the topsheet and the standing gathers that overlap with the crotch portion of the absorbent article.

7. The absorbent article according to claim 6, wherein the parts of the sheet material of the topsheet and of each standing gather are arranged next to or in overlap with each other, at least when the absorbent article is worn by a wearer.

8. The absorbent article according to claim 1, wherein the backsheet comprises a sheet material that has a stiffness from 2.0 to 20 mm/N as measured according to the softness test method, and wherein the backsheet sheet material has a softness of 16 or less as measured on a surface of the backsheet sheet material and according to the softness test method.

9. The absorbent article according to claim 8, wherein the sum of the stiffness of the backsheet sheet material and the stiffness of the standing gather sheet material of is 4.5 mm/N or more.

10. The absorbent article according to claim 8, wherein the sum of the softness the backsheet sheet material and the softness of the standing gather sheet material is 19 dB V^2 rms or less.

11. The absorbent article according to claim 8, wherein the difference between the stiffness of the sheet material of the backsheet and the stiffness of the standing gather sheet material is 0.8 mm/N or less.

12. The absorbent article according to claim 8, wherein the sheet materials of the backsheet and of each standing gather at least form parts of the backsheet and the standing gathers that overlap with the crotch portion of the absorbent article.

13. The absorbent article according to claim 12, wherein the parts of the sheet material of the backsheet and of each standing gather are arranged next to or in overlap with each other.

14. The absorbent article according to claim 8, wherein the backsheet sheet material comprises a nonwoven material of fibres.

15. The absorbent article according to claim 14, wherein nonwoven material of the backsheet sheet material comprises polyolefin-containing fibres.

16. The absorbent article according to claim 14, wherein the fibres of the backsheet sheet material contains a slip agent.

17. The absorbent article according claim 14, wherein the nonwoven material of the backsheet sheet material comprises a layer of a nonwoven web with a side surface, wherein the polyolefin fibres are bound together by an alternating bonding pattern having a total bonded surface area of from 5 to 30% of the total surface area of the side surface.

18. The absorbent article according to claim 14, wherein the nonwoven material of the backsheet sheet material comprises a layer of spunbond material.

19. The absorbent article according to claim 14, wherein the nonwoven material of the backsheet sheet material comprises a layer of meltblown material.

20. The absorbent article according to claim 19, wherein the nonwoven of the backsheet sheet material comprises two outer layers of a spunbond material and an intermediate layer between the outer layers that is of a meltblown material.

21. The absorbent article according to claim 20, wherein the polyolefin fibres comprises polyethylene.

22. The absorbent article according to claim 14, wherein the polyolefin fibres are bicomponent fibres.

23. The absorbent article according to claim 1, wherein the standing gather sheet material is configured to be a leakage barrier material, and wherein the topsheet sheet material is configured to be an inlet material.

* * * * *